United States Patent [19]
DeBusk et al.

[11] Patent Number: 5,995,937
[45] Date of Patent: Nov. 30, 1999

[54] MODULAR HEALTH-CARE INFORMATION MANAGEMENT SYSTEM UTILIZING REUSABLE SOFTWARE OBJECTS

[75] Inventors: Brian C. DeBusk, Clinton; Michael C. Cofer, Knoxville; Mark W. Shanks, Clinton; Wil Francis Lukens, Knoxville, all of Tenn.

[73] Assignee: DeRoyal Industries, Inc., Powell, Tenn.

[21] Appl. No.: 08/965,788

[22] Filed: Nov. 7, 1997

[51] Int. Cl.⁶ .................................................. G06F 17/60
[52] U.S. Cl. ................. 705/2; 705/8; 705/9; 364/468.05
[58] Field of Search ..................... 705/2, 3, 1, 8, 705/9, 7; 364/468.05

[56] References Cited

U.S. PATENT DOCUMENTS

| | | | |
|---|---|---|---|
| 4,174,598 | 11/1979 | Shepherd et al. | 53/431 |
| 4,737,910 | 4/1988 | Kimbrow | 364/403 |
| 4,987,538 | 1/1991 | Johnson et al. | 364/401 |
| 5,001,630 | 3/1991 | Wiltfong | 364/401 |
| 5,072,383 | 12/1991 | Brimm et al. | 364/413 |
| 5,168,445 | 12/1992 | Kawashima et al. | 364/403 |
| 5,235,795 | 8/1993 | DeBusk | 53/467 |
| 5,287,267 | 2/1994 | Jayaraman et al. | 364/403 |
| 5,295,067 | 3/1994 | Cho et al. | 364/401 |
| 5,301,320 | 4/1994 | McAtee et al. | 705/9 |
| 5,307,261 | 4/1994 | Maki et al. | 364/401 |
| 5,319,543 | 6/1994 | Wilhelm | 705/3 |
| 5,321,605 | 6/1994 | Chapman et al. | 364/402 |
| 5,325,293 | 6/1994 | Dorne | 364/413 |
| 5,359,509 | 10/1994 | Little et al. | 364/401 |
| 5,412,576 | 5/1995 | Hansen | 364/468 |
| 5,517,405 | 5/1996 | McAndrew et al. | 364/401 |
| 5,557,514 | 9/1996 | Seare et al. | 364/401 |
| 5,583,758 | 12/1996 | McIlory et al. | 705/2 |
| 5,596,502 | 1/1997 | Koski et al. | 364/468.01 |
| 5,610,811 | 3/1997 | Honda | 395/202 |
| 5,671,362 | 9/1997 | Cowe et al. | 395/228 |
| 5,682,728 | 11/1997 | DeBusk et al. | 53/445 |
| 5,721,913 | 2/1998 | Ackroff et al. | 707/103 |
| 5,727,161 | 3/1998 | Purcell, Jr. | 395/207 |
| 5,732,401 | 3/1998 | Conway | 705/29 |
| 5,748,907 | 5/1998 | Crane | 705/2 |

(List continued on next page.)

FOREIGN PATENT DOCUMENTS 0 556 093 A1  4/1993  France .

OTHER PUBLICATIONS

Sethi, Ravi. Programming Languages. New York: Addison Wesley. 1989, pp. 169–173 and 178–185.
Biggerstaff et al. Software Reusability. New York: Addison-Wesley. 1989, vol. 2, pp. 269–287, especially pp. 280–284.

*Primary Examiner*—Emanuel Todd Voeltz
*Assistant Examiner*—George D. Morgan
*Attorney, Agent, or Firm*—Luedeka, Neely & Graham PC

[57] ABSTRACT

Disclosed is a health-care information management system that utilizes modular and reusable software objects to allow for user configuration. The disclosed information management system allows for the creation by the user software objects representative of specific events and resources which will occur or be utilized during the provision of health-care to patients. These user configured software modules then allow the user to track the provision of health-care, the utilization of resources during the provision of health-care, the allocation of resources to perform medical procedures and identify opportunities for enhancing efficiencies in the provision of health-care services. In on embodiment of the invention described, the system allows for the user to create, manage and maintain software modules representing specific clinical pathways to be performed in a health-care institution. The user creates these modules using user configurable software objects that function to represent containers, resources and data. The software objects are modular and re-usable and allow the user to select components for creation of the modules. The created modules may then be used to provide information management relating to the provision of the medical procedures represented by the clinical pathway modules.

6 Claims, 2 Drawing Sheets

U.S. PATENT DOCUMENTS

| | | | |
|---|---|---|---|
| 5,752,234 | 5/1998 | Withers | 705/2 |
| 5,771,172 | 6/1998 | Yamamoto et al. | 364/468.13 |
| 5,777,877 | 7/1998 | Beppu et al. | 364/468.03 |
| 5,826,239 | 10/1998 | Du et al. | 705/8 |
| 5,835,910 | 11/1998 | Kavanagh et al. | 707/103 |
| 5,842,173 | 11/1998 | Strum et al. | 705/1 |
| 5,845,254 | 12/1998 | Lockwood et al. | 705/2 |

MODULAR HEALTH-CARE INFORMATION MANAGEMENT SYSTEM UTILIZING REUSABLE SOFTWARE OBJECTS

FIELD OF THE INVENTION

This invention relates to the field of information systems for use in the health-care environment and in particular to an information system incorporating software for supply, scheduling and resource utilization management in the health-care environment.

BACKGROUND OF THE INVENTION

In the provision of medical services, one way of describing the process by which medical services are provided is through the concept of a clinical pathway. Any given treatment regime or clinical procedure, may be easily described as a related series of care events. Each care event has a some relation to the preceding and/or following care events that is logical and reasonable. For example, take a simple procedure such as suturing a wound. The task of suturing a wound can be described as a series of care events: 1) examination of the wound; 2) cleansing of the wound; 3) anesthesia; 4) suturing of the wound; and 5) dressing the sutured wound. Thus, each of these related care events, make up a clinical pathway for the procedure of suturing a wound. To a person familiar with the medical environment, it will be apparent that each of the care events could be broken down into a more detailed series of sub-care events, thus, the concept of the clinical pathway is scaleable; that is, any given care event may be made of a series of care events and can therefore be described as a clinical pathway.

The concept of the clinical pathway may also be expanded to more involved procedures. For example, a patient might go to her doctor complaining of particular symptoms. The doctor might then make an examination, or order tests. Based upon the result of the examination and/or tests, the doctor would make a diagnosis and prescribe a treatment regime. Assume that the treatment regime included a surgical procedure to be performed in a hospital, as well as follow-up care. In this case, the clinical pathway might look like: 1) patient induction (basic administration getting the patient into the doctor's system); 2) examination; 3) testing; 4) diagnosis; 5) prescription of treatment; 6) admission to the hospital; 7) pre-surgical testing; 8) pre-operative preparation; 9) anesthesia; 10) surgery; 11) post-operative recovery; 12) discharge from hospital; 13) follow-up treatment; 14) final discharge. Once again, it is obvious that each care event in the given example might be further broken down into smaller incremental care events and, thus, represent a clinical pathway of its own. For example, the surgery could be broken down into each step associated with the surgery from the initial incision until the incision is closed.

In addition to the fact that each care event represents the provision of some type of medical (or administrative) service, each care event will also require the allocation of some type of resources in order to be performed. These resources may be in the form of labor (doctor, nurse, technician, data clerk, etc.), equipment (x-ray machine, respirator, vital signs monitors, etc.), or supplies (sponges, surgical instruments, drapes, x-ray film, sutures, medications, etc.). Thus, for each care event it is possible to identify the allocation of resources necessary for completion of the care event. For example, for the examination step described in the second example, the allocation of resources could be: 15 minutes of doctor's time, use of a specimen collector, use of a specimen container, and the use of a blood collection kit. Likewise, the testing step might include the use of an imaging device (such as an x-ray or MRI machine), 30 minutes of technicians time, use of x-ray film, use of an x-ray developer and associated chemical supplies, and 15 minutes of a radiologist's time to interpret the images.

By describing events in the context of a procedural pathway, a framework is provided which allows for the systematic classification of the steps necessary to treat a particular patient as well as identifying the resource allocation necessary to properly complete the clinical pathway. In the current healthcare environment of cost control and containment, the use of the clinical pathway framework provides an effective and efficient method for characterizing and analyzing the provision of health-care services in the clinical environment.

One important consideration in the provision of healthcare is the allocation, utilization and consumption of resources such as labor, durable equipment, reusable supplies and disposable supplies. The provision of medical supplies for use in the clinical environment, most particularly in the hospital environment, has evolved through over time as the nature of health care provision and, importantly, cost reimbursement, has changed. For example, in the past, the most common way for supplies to be obtained by hospitals was for a central supply service to order the individual supplies anticipated to be needed for a given time period. These supplies would be maintained in a supply room until needed for a given procedure. Once a procedure had been scheduled, a pick list (a list of supplies) would be generated based on the procedure and the doctor performing the procedure. A hospital employee would then use the pick list to withdraw the desired items from inventory and place them in the operating room where the procedure would take place. After the procedure was completed, unused supplies would be returned to inventory, a list of used supplies provided to the billing department, and the used supplies disposed of or re-sterilized. However, this system was costly and inefficient.

For example, a relatively large inventory of supplies had to be maintained, particularly for standard items such as drapes, sponges, sutures, clamps, etc., which could be used in a large variety of procedures. The inventory of such items had to be large in order to insure that sufficient quantities were on hand for every procedure. Furthermore, the act of picking items for surgery and, later, restocking unused items, was onerous and expensive since relatively highly skilled labor was utilized to insure that the proper items were collected and that the restocked items were placed in the proper location. In particular, the restocking of unused items was a substantial burden on the hospital. Due to the then current mode of reimbursement for supply costs each item pulled from inventory had to be either used (and billed for) or restocked (and not billed for). If an item was not used during the procedure and was billed for anyway, the billing for that product could be considered fraud on the reimburser. Since items were often individually wrapped, the restocking procedure could be very time consuming, particularly where sufficient quantities of items were picked from inventory to cover any situation during surgery (i.e., it would not be uncommon to withdraw 10 clamps from inventory and use only 3 or 4, except in situations where heavy bleeding is encountered, which might necessitate the use of all 10).

This situation led to the development of the procedural pack. Initially, suppliers started noting that certain combinations of supplies were used in almost all surgeries. For example, a series of drapes would almost always be used. Thus, a procedural drape pack was developed which included a collection of the most commonly used drapes in numbers commonly used. These drapes were packaged and sterilized as a unit, so that the use of any portion of the unit constituted use of the entire unit. For example, the pack might contain 5 drapes, but only four might be used during surgery. However, since the package was opened, and sterility was thereby compromised, the entire unit could legitimately be considered used. Although some waste occurred, this system cut out the required re-stocking cost.

Initially, small procedural packs and packs were developed for common events. Incision packs, anesthesia packs, suture kits and a variety of other procedural packs, or supply bundles, were developed. As hospitals grew more used to the concept of procedural packs and packs, the demand for more comprehensive supply bundles increased. The procedural pack or pack ultimately evolved into a large bundle, differentiated by surgical procedure, that included all disposable components for that procedure.

In the era of cost—plus reimbursement, the hospitals had an incentive to use ever growing, comprehensive procedural packs. Use of a large pack, with all possible components present, served to minimize the amount of labor required to pick items from inventory and restock unused item. Additionally, it allowed hospitals to greatly reduce their inventory since such packs could be ordered on an as-needed basis, instead of maintaining a large inventory supplies. However, in order to increase these efficiencies, the packs had to be able to cover any possibility that might reasonably be encountered during the procedure, and often included a large amount of supplies which were not often used in most procedures.

With the advent of cost-containment in the health-care environment, the care providers are required by the reimbursers, to minimize expense and cost wherever possible. Under the tenets of managed care, if a supply is not used during a procedure, then the reimburser is not willing to pay for that supply. This environment leads back toward the concept of having an inventory of supplies which are pulled and then restocked when unused. However, reimbursers do realize that some waste in the use of supplies is justified in order to minimize labor expenses concerned with the pulling and restocking of supplies. Thus, the pressure on suppliers led to the development of "custom procedural packs." These custom packs attempt to be comprehensive, but are tailored to the circumstances to attempt to minimize waste. For example, there is a "parts list" or supply list generated by each doctor for each procedure performed by that doctor in a given hospital. Thus, doctors are able to specify the supplies desired, the quantities desired and, if a preference is felt, the brand and type of the desired supply. Thus, if Doctor A uses more lap sponges than Doctor B, their preference cards will differ. Under the cost-plus reimbursement scenario, a procedural pack would have been developed which just had the maximum number of lap sponges used by any doctor. The extra lap sponges in a pack provided to Doctor B would just be wasted. However, under managed care, a custom procedural pack could be developed for Doctor A and Doctor B which allowed for the differing preferences. Once again, however, the more specialized the custom procedural pack, the more inventory will have to be maintained. Since there is the potential for each doctor to have a different custom procedural pack for each different procedure performed by the doctor, there would be no standardization of packs in inventory and, therefore, a number of each custom procedural packs would be required for each doctor.

In the final analysis, a balance must be met between standardization of procedural packs, which will allow for the greatest savings in inventory, because more standardized packs can be used for more different doctors and procedures, and customization which minimizes the waste developed due to usage differences from doctor to doctor and procedure to procedure. It will be apparent to one skilled in the art that the proper balance of standardization and customization will result in the minimum of cost, by minimizing both waste and inventory. Thus, with proper balancing, both the reimburser will save money, due to decreased waste, and the care provider will save money, due to inventory control.

Custom procedural packs have been present in the medical supply industry almost since the inception of the procedural pack. As a marketing technique, the pack manufacturers were willing to customize packs to gain a competitive advantage over other manufacturers and gain an entree to new accounts. However, recently, the industry has become more sophisticated in developing custom packs and packs with the cooperation of the customers. Initially, custom procedural packs were slight variations of standard packs or packs already offered by the manufacturer. However, with increasing customization demands and ever changing product offerings, a more sophisticated method of developing custom procedural packs was required.

One approach to the problem is described in U.S. application Ser. No. 08/889,948, filed Jul. 10, 1997, entitled Method for the Supply of Medical Supplies to a Health-care Institution Based on a Nested Bill of Materials on a Procedure Level, which is a continuation in part of U.S. Pat. No. 5,682,728, issued Nov. 4, 1997, entitled, Method for the Supply of Medical Supplies to a Health-care Institution Based on a Nested Bill of Materials on a Procedure Level, the entire specification of which is hereby incorporated by reference. As may be seen in this application, using the clinical pathway approach described above, each medical procedure may be described as a series of procedures to be performed in a specified order. Thus, at each step in the clinical pathway, the supplies needed to complete that step can be expressed as a supply bundle (or bundles) which will be utilized during that step. Thus, using the clinical pathway model, a nested bill of materials for a given clinical pathway, at the procedural level, may be generated to develop a supply list for the contents of a custom procedural pack. The clinical pathway model allows for an easier approach to analyzing the supplies which will be needed at each step, since it provides a break-down of each phase of a medical procedure.

The procedure for developing the types of custom procedural packs described herein will include some starting point based upon historical usage. For example, say that the hospital already has a standard procedural pack for a laparoscopic gall bladder surgery. The supply list for this standard procedural pack could provide the template for developing the custom procedural packs for that hospital. After first organizing the template supply list into a nested bill of materials as described in the above referenced application and patent, the template would be modified by each doctor's preference card to develop a custom nested bill of materials for each doctor who performs that procedure in the hospital. The step of organizing this initial bill of materials for each doctor will require some judgment in order that minor differences in supply usage are minimized (i.e., if one doctor uses 2 units of a low cost item, and another doctor uses 3 units of the same item, it is probably cheaper to standardized both bills of materials to 3 units; conversely, if the item is a high cost item, it is best to differentiate the bills of materials). The result is that a bill of materials for a procedural pack is developed for each doctor for each procedure.

With a bill of materials developed for each procedural pack for each procedure, the various suppliers of the products can then develop supply bundles for each step set out in the clinical pathway. Typically, not all of the supplies will be provided by a single supplier or manufacturer, so that, as described in the above-referenced application and patent multiple supply sources will develop supply bundles for inclusion into the procedural pack for a given customer. As described in that application, a container may be shipped to each source of supplies and the supplies provided by that source can be added to the container, thus reducing the time and shipping costs associated with collecting and shipping various components to a single assembly location. In operation, the initial source of the container would develop a work order based on the nested bill of materials which each supplier would use to add the appropriate supply bundles to the container. Alternatively, each supplier could ship its supply bundle to a centralized assembly location for assembly of the container and shipment to the ultimate customer. This supply paradigm provides the customer and the suppliers with a framework within which the suppliers can respond very rapidly to an order by the hospital for a custom procedural pack. Thus, even though there exists the possibility that a large number of different packs may be developed for each hospital, the hospital need not maintain a large inventory of such custom procedural packs since the supply process has been streamlined. With proper implementation of the system, a very small number of custom procedural packs may be kept in inventory by the hospital (maybe one week's worth) which will obviously reduce the inventory costs of the hospital. Similarly, since the parts list, or nested bill of materials for each pack has been analyzed, waste is minimized and efficiency is enhanced.

In this supply paradigm, which has been implemented by the assignee hereof, DeRoyal Industries, Inc., under the trademark and service mark TRACEPAK, an attempt is made at the time of the development of the nested bill of materials for each custom procedural pack to minimize waste while maximizing standardization to ultimately reduce the overall cost to the care provider. However, this initial analysis is not sufficient to insure that the bill of materials remains optimized. For example, doctors are constantly revising their supply usage based upon new surgical techniques. Similarly, manufacturers are constantly updating their products to incorporate new products and developments. Also, prices are constantly changing in the marketplace.

Upon review of the foregoing, there are several areas where intervention is necessary to insure that the process results in the best balance between waste minimization and standardization, in addition to the ultimate requirement that all of the supplies required during a procedure are actually available when the procedure is conducted. First, the clinical pathway must be developed. Second, bills of materials must be developed in the context of the clinical pathway and balanced to account for doctor preferences, standardization and waste minimization. Finally, usage of materials must be tracked in order to insure that the bills of materials currently in use are optimized to continue to minimize waste while maximizing standardization, as well as providing a basis for documenting resource usage during a procedure in order to allow for proper billing of the procedure to the party responsible for paying for the procedure.

An additional element that must be considered in the clinical pathway is not only the optimization of the bill of resources through utilization review and standardization, is the scheduling of the resources so that the proper resource is in the proper location at the proper time. Prior art methods of scheduling resources have been organized around OR scheduling programs such as the OR scheduling program available from DeRoyal Business Systems, LLC, an affiliate of the assignee hereof. This software is typical of OR scheduling software in that it provides a calendaring function for reserving OR's for use by doctors and allows for the scheduling of various related items such as durable medical equipment, etc. Also, some OR scheduling packages provide a database function for maintaining doctor "preference cards," which are lists of specific supplies that a given doctor will require during the surgery.

However, such software, usually marketed as a stand-alone package, does not function under the clinical pathway management and is not integrated with resource management. Thus, information is typically unnecessarily entered multiple times, in multiple locations, on multiple information systems. For example, a bill of materials may be generated for a given medical procedure for use by the supply department of a hospital in order to insure that the needed supplies will be available; separately, the doctor preference card from the OR scheduling package will be used to make sure that the supplied materials matches the doctor's preferences; the availability and provision of labor resources will be handled by a different department with a different information system. Usually, these information systems are not integrated and their use results in a myriad of duplication of data entry, along with substantial opportunities for error. Finally, these information systems do not typically provide a basis for calculating medical procedure costs in an efficient manner, so that cost recovery and cost reductions processes must be done on an ad hoc basis.

Returning to the top level of the clinical pathway analysis, the performance of a medical procedure represented by the clinical pathway requires that all of the necessary resources be brought together at the appropriate time and place, which requires that supplies be accounted for and personnel and other resources be scheduled. Once the procedure has been performed, it is important that resource consumption/utilization be recorded for the purposes of cost recovery and utilization review. Finally, it is important that the information be available for analysis in order to allow the process to be analyzed in order to facilitate more efficient resource utilization and to identify economies which may be realized in the clinical pathway.

To date, no hospital information system provides an integrated package for OR scheduling/preference card management, resource consumption logging/storage and resource utilization analysis/bill of resource standardization. Furthermore, even the most comprehensive hospital information systems are written in monolithic style which either represents a 100% custom application written specifically for the customer, or an off-the-shelf application that does not meet all of the needs of the customer. Neither situation fits the current health-care environment of reform, cost-cutting and change. Monolithic software packages require the review and revision of large blocks of source code and a small change at one point may well affect the functioning of other portions of the code. In large applications, hundreds of thousands, if not millions, of lines of code must be reviewed for every change, even if relatively minor. This state of affairs often results in health-care institutions refusing to adopt cost-saving and efficiency enhancing measures, since the potential benefits are often outweighed by the cost and problems which would be involved in adapting their current information systems to the better processes. Also, since different institutions are different sizes, serve different populations, use different doctors, have different areas of core competency, etc., the one size fits all approach to off-the-shelf information systems often results in some institutions adopting procedures which, while they may work well in some environments, aren't the most efficient for that institution just to enable the use of a given information system. However, such a system is in actuality backwards, the institution should be able to determine the most efficient way to operate and then have an information system which is adaptable, at no great expense, to the needs of the institution.

It is therefore an object of the present invention to provide an integrated information system for use in healthcare institutions for managing, optimizing and analyzing the use of resources within that institution.

It is yet a further object of the present invention to provide an integrated information system for us in healthcare institutions for managing, optimizing and analyzing the use of resources within that institution utilizing a modular, component-ware software structure.

It is yet a further object of the present invention to provide an integrated supply, scheduling, and resource utilization management system for use in the health-care environment.

SUMMARY OF THE INVENTION

The above and further objects are met in the preferred embodiment of the present invention. In the preferred embodiment of the present invention, there is provided a health care information management system. In the preferred embodiment, the information management system runs from either a stand-alone or network personal computer running commercially available operating systems and database software. The general purpose computer has memory for data storage, at least one central processing unit, a display and user input devices such as a keyboard and/or mouse. In the preferred embodiment the information management system is installed on the general purpose computer and operates to collect, store, maintain and manage healthcare related information.

In the preferred embodiment of the present invention the information management system is comprised of individual software objects which can communicate with each other in order to facilitate the information management function of the system. The software objects are configurable by the user to represent health-care related procedures in a fashion that allows for the development of custom software modules representative of the procedure for which information is to be managed.

In the preferred embodiment there is provided node software objects that provide for the creation, management and maintenance of module software objects corresponding to the type of information to be managed. The software module objects are user created objects which represent individual templates for medical procedures or the like. Using the functionality of the software module objects and the node software objects the user may select container, resource and data software objects to populate the module software objects.

Container software objects function to contain other container, resource or data software objects and allow other software object to be grouped by common characteristics. Resource software objects represent individual resources to be used in the procedure the module represents. Resource software objects may be used to represent items such as supplies, equipment, personnel, pharmacy items or the like. Data software objects are placed in the module wherever specific information may need to be collected or used. These objects are designed to gather and store specific information related to the module or container with which they are associated.

In a further preferred embodiment of the preferred embodiment of the present invention, one type of node software object functionality is to allow the user to create clinical pathway modules that represent a given clinical procedure. The clinical pathway modules would include container, resource and data objects that represent the clinical procedure to be performed. In this embodiment, container objects are used to represent discrete care events that are part of the clinical pathway. Other containers representing bundles of resources may be added to the care event containers as well as resource objects that represent resources to be utilized in performing the care event represented by the care event container. Data objects may also be included at various locations in the module to collect and manage data that is specific to a particular location in the clinical pathway.

In the preferred embodiment of the present invention, the user may create the various container, resource and data objects that will be used to create the module representing a given clinical pathway. Alternatively, the user may select such objects from pre-configured libraries of such objects or by copying such objects from clinical pathways already created.

In a further preferred embodiment of the present invention, a node for tracking resource utilization in individual patient cases may be provided. This case node software allows the user to create case modules by selecting an already configured procedural pathway and adding patient and doctor specific information to it. In the node, the user may then easily input information concerning the usage of the resources populating the clinical pathway and maintain a history of resource usage, costing information and/or clinical outcome. This information provides for a historical database of resource utilization which may be used to provide information on the cost of medical procedures, identify waste in the performance of the procedures, track and capture cost information or a variety of other uses.

In a further preferred embodiment of the present invention, the information generated by the case node functionality may be used by a standardization node to generate models of individual cases, previously created, for use in analyzing utilization. Each case to be studied would be converted into a model module by this node and collectively the desired cases would be collected into a study module. This study module would then be subject to the functionality of the standardization node to be analyzed for standardization opportunities, cost comparison studies or a variety of other comparisons designed to allow the user to better track and optimize resource utilization.

In all of the functions described above, the software object approach is maintained. Under each node the user would still create modules which further include container, resource and data objects representative of real items in the provision of health-care services. To the extent that objects from one node are used by another, they are copied and their functionality will depend upon the functionality of the node to which they are copies.

BRIEF DESCRIPTION OF THE DRAWINGS

The foregoing embodiments of the present invention may be best understood with reference to the following Detailed Description of the Preferred Embodiments and the drawings in which.

DETAILED DESCRIPTION OF THE PREFERRED EMBODIMENTS

Figure 1:
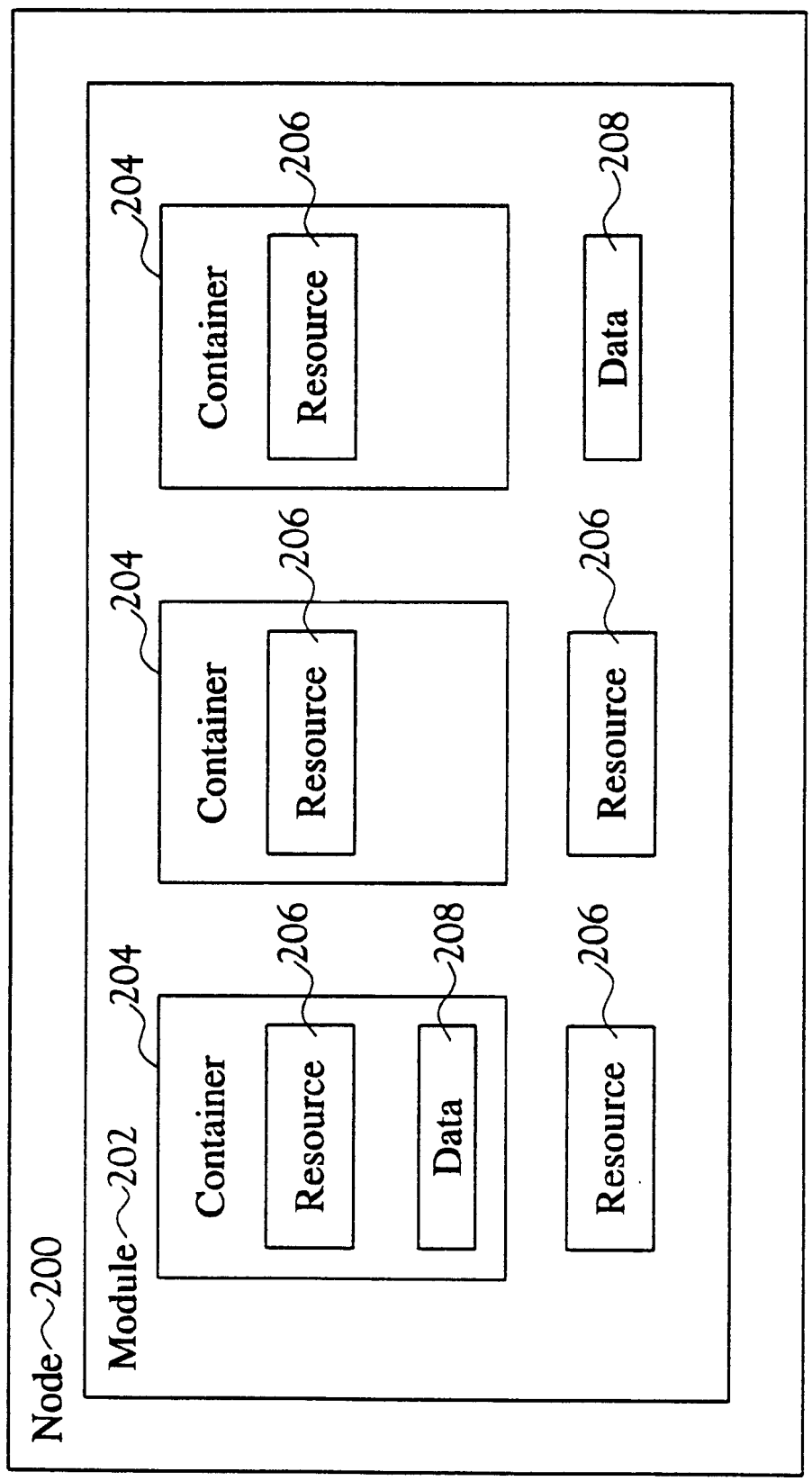
FIG. 1 is a block diagram showing the generic form of the present invention.

Before referring to the Figures, some background information concerning the functioning of data systems in the health-care environment is in order. Typically, these information systems have used the paradigm of the patient record in managing information. That is, the primary identifying feature was the patient for information which was stored about resource allocation, supply utilization, resource scheduling, supply ordering, cost accounting, etc. Obviously, this paradigm has worked for some time owing in large part to the fact that cost reimbursement is done on a per patient basis and all cost recovery and accounting needed to be allocable to an individual patient.

However, as health-care reform debate has forced health-care providers to focus on streamlining the provision of medical services, the focus has turned from patient centered information systems to procedure based management and accounting. For example, DeRoyal Industries, Inc., the assignee of U.S. patent application Ser. No. 08/846,798, filed Apr. 30, 1997, entitled, Method and System for the Tracking and Profiling of Supply Usage in a Health Care Environment, U.S. patent application Ser. No. 08/936,780, filed Sep. 24, 1997, entitled Method for the Analysis and Standardization of Bills of Resources, and U.S. application Ser. No. 08/889,948, filed Jul. 10, 1997, entitled Method for the Supply of Medical Supplies to a Health-care Institution Based on a Nested Bill of Materials on a Procedure Level, which is a continuation in part of U.S. Pat. No. 5,682,728, issued Nov. 4, 1997, entitled, Method for the Supply of Medical Supplies to a Health-care Institution Based on a Nested Bill of Materials on a Procedure Level, the entire disclosures of which are hereby incorporated by reference thereto as if fully set forth herein, has been developing a resource utilization paradigm based upon the concept of the clinical pathway described in the Background. Basing an information system around the procedural pathway, as opposed to just tying services, supplies and other resources used to the patient, with no real relation to the pathway, provides an inherent ability to use the information more efficiently and to allow for greater cost accountability in the provision of medical services.

To illustrate the efficiency of the procedural pathway, it is best to analyze generally a hospital stay for a given patient. Initially, the patient will be admitted, have some bloodwork done, be assigned a room, possibly be subject to some diagnostic screenings, possibly have a procedure done, spend a period of time recovering from the procedure and be discharged. Also, the clinical pathway may extend beyond the hospital stay and include follow-up care such as periodic check-ups and/or rehabilitation. Each step along the procedural pathway can be broken down into increasingly fine detail as series of more and more detailed sub-procedures. For example, the surgical procedure can be further broken down into surgical prep, anesthesia, the surgical procedure, closing and post-op anesthesia recovery. Obviously, each of these sub-procedures could be further broken down into specific tasks to be performed at each stage.

As can be seen from the procedural pathway model, each stage of the procedural pathway is going to require the utilization of resources. These resources may be labor resources, consumable supply items, durable equipment, reusable supply items, particular rooms (i.e. patient rooms, Operating Rooms (OR's), recovery rooms, etc.) or services. For example, the bloodwork will require a technician to draw the blood, the disposable equipment for drawing blood, a labor resource to deliver the blood to the laboratory, the consumable and reusable supplies for handling and testing the blood, durable medical equipment for testing the blood, labor resources for testing the blood and generating the report, and a labor resource for providing the report to the patient's chart. As can be seen, each resource can be analyzed and tied to a particular care event along the procedural pathway.

Each procedural pathway is going to have some unique characteristics which will vary based upon the reason the patient is in the health-care facility (the type of procedure), the doctor performing the procedure and the characteristics of the patient. Obviously, the clinical pathway is different from someone having heart-bypass surgery from someone having out-patient orthopedic surgery. Likewise, preferences vary from one doctor to another in performing the same surgery; i.e. one doctor may prefer the feel of on brand of scalpel while another doctor may prefer another. Finally, the patient will often dictate variation within a given procedure; i.e. one patient may have certain physical characteristics that require using certain supplies and equipment and another patient may require different supplies and equipment.

The present invention provides an information system for use in the health-care environment that utilizes the procedural pathway paradigm for the input of data, the organization of data, the retrieval of data and the analysis of the data. In addition to storing unique data for each clinical pathway (historical data), the present invention also provides for the development of clinical pathways for certain medical procedures which have been analyzed and standard pathways developed. These clinical pathways, which are created from modular software objects configured by the user of the software associate the anticipated resource allocation to a given procedure and allow for the anticipation of resource consumption for each upcoming standard procedure. For example, if a clinical pathway has been developed for a hip replacement surgery, the clinical pathway for a given patient coming in for hip surgery is easily developed from the template. The information system user would merely need to enter the identifying information about the patient and the surgeon performing the procedure, and the standard template would generate a clinical pathway showing the resources that should be required for that patient. At a further level of detail, departure points from the standard template can be identified and the alternate resource allocation for the departure points may also be provided in the information system. For example, in copending application Ser. No. 08/846,798, the disclosure of which has been incorporated by reference, this feature is described as a conditional bundle. For example, in the hip replacement surgery described above, variations in resource requirements may vary from doctor to doctor because of differing techniques, requirements and subjective preferences. Thus, the standard template for a hip replacement surgery may be substantially the same for two different doctors, but vary on a few items. The conditional bundles can be used to account for the departure from the standard template for each doctor and, by entering the doctor performing the procedure, the information system can automatically associate the appropriate conditional bundle with the standard template to form the clinical pathway for a given patient.

In terms of resource management, there are two basic types of resources which will be needed to perform a medical procedure at a given location: 1) those resources which will need to be brought in from outside the location for the procedure and 2) those resources which are maintained by the location and which must be scheduled for a given procedure (for the purposes of this application, although doctors are not usually employed by the hospital, we will assume that they are resources associated with the location, since they are typically driving the scheduling of a procedure at a location). The management of outside and inside resources requires the consideration of two different sets of problems. Typically, the outside resources will primarily include the supplies which must be ordered from outside vendors, be delivered to the location and be provided at the appropriate time and place for the performance of the procedure. The inside resources will include the labor resources, equipment owned and maintained by the location and facilities at the location such as OR's, radiology, laboratories, etc.

In managing the outside resources there are two competing interests, the desire to have sufficient quantities of everything readily available, which would necessitate a large inventory of supplies along with skilled personnel to maintain the inventory and deliver it for performance of the procedure, and the desire to minimize inventory, which minimizes inventory carrying costs, the risk that inventory will expire before use, tied-up capital and the skilled labor necessary to maintain the inventory and pull it for each procedure.

In managing inside resources the goal is to maximize the utilization of each available resource while carrying only the minimum amount of required resources to get the job done. Management of these resources necessitates that efficient resource allocation tools be used so that the location is not carrying costs associated with labor, equipment and facilities which are not being fully used, while insuring that all of the procedures can be performed in a timely fashion. For example, idle employees, equipment, OR's, etc. all carry a substantial cost. However, overworked employees, overused equipment and overbooked facilities reduce the efficiency and efficacy of the performance of the procedures and result additional costs. Thus, precise scheduling and resource utilization management software is necessary to allow for the maximum productivity from resources, while minimizing inefficiency caused by overbooked resources and overworked employees. Additionally, software which allows for the detailed analysis of historical resource utilization will allow for the prediction of when new labor and other resources will be needed and allow for the most effective way of acquiring those resources, often saving money as opposed to the last minute recognition and rush acquisition of such resources.

DESCRIPTION OF THE PREFERRED EMBODIMENT

In the preferred embodiment, the information management system consists of a series of software objects implemented using Microsoft ActiveX® controls which may be configured and linked by a user to build a custom configured health-care information management system. Preferably, the information system is implemented on a Windows NT® or Windows 95® based personal computer, which may or may not be networked. In order to maintain a database of information related to this information system, a database program such as Microsoft SQL/Server® or Microsoft Access® is used in background. The information system of the preferred embodiment generates data and communicates through an interface compatible with the background database program. Typically, the software objects which will be described are coded in Visual C++ or Visual Basic, and adhere to the framework of ActiveX® or OLE controls so as to maintain the ability to be implemented as compatible software objects in a component based software architecture.

In general, the software provides a number of "nodes," each of which correspond to a particular function of the information system. For example, if the system will have functions for developing and maintaining software based clinical pathways, maintaining and logging resource consumption on a case by case basis, and studying resource consumption for logged cases, each of these functions would represent one node. Each of these nodes uses the feature of ActiveX® controls to allow objects created in one node to provide necessary information or form the basis for a new object in another node. The interaction of objects from one node to another will be described more fully hereinafter.

Referring now to FIG. 1, each node 200, as described, provides for a particular information management function in the present invention. Also, each node 200 represents a software object which will allow the user to perform certain functions and tasks relative to the information system function provided for the node 200. In general, the function of each node will be to allow the user to generate specific templates, or software object modules 202 which will organize additional software objects into custom configurations representative of the information to be managed. Under each node 200, the user will have access to further software objects, by copying from previously generated templates, by creating the objects or from an object library, in order to access the functionality of the node 200. The software objects available to the user will be of three specific types: 1) container objects 204, 2) resource objects 206 and 3) data objects 208. Each of these objects represent ActiveX® software objects which function as miniature software programs to perform a specific function. Container objects 204 function as receptacles of other objects and act to organize the other objects in accordance with the user's specifications. Additionally, container objects 204 will be customized by the input of data from the user based upon what the container object 204 is designed to hold, the specific use to which the container object is subjected by the user and other usage specific data which the user will provide.

Resource objects 206 are software objects which represent resources to be utilized in the provision of the healthcare. Resource objects 206 typically represent supplies, or kits of supplies, equipment, personnel, pharmaceuticals, or any other resource which will be utilized during the provision of healthcare. Each resource object 206 will be populated with data relevant to that object and will communicate that information as required.

Data objects 208 are software objects which will be used by the user to collect specific information for use by the template or the information system. For example, it may be necessary to gather certain procedure specific information at some point in a clinical pathway and a data object 208 may be inserted at that point in a module 202 to collect such data and make it available to the appropriate software objects.

Figure 2:
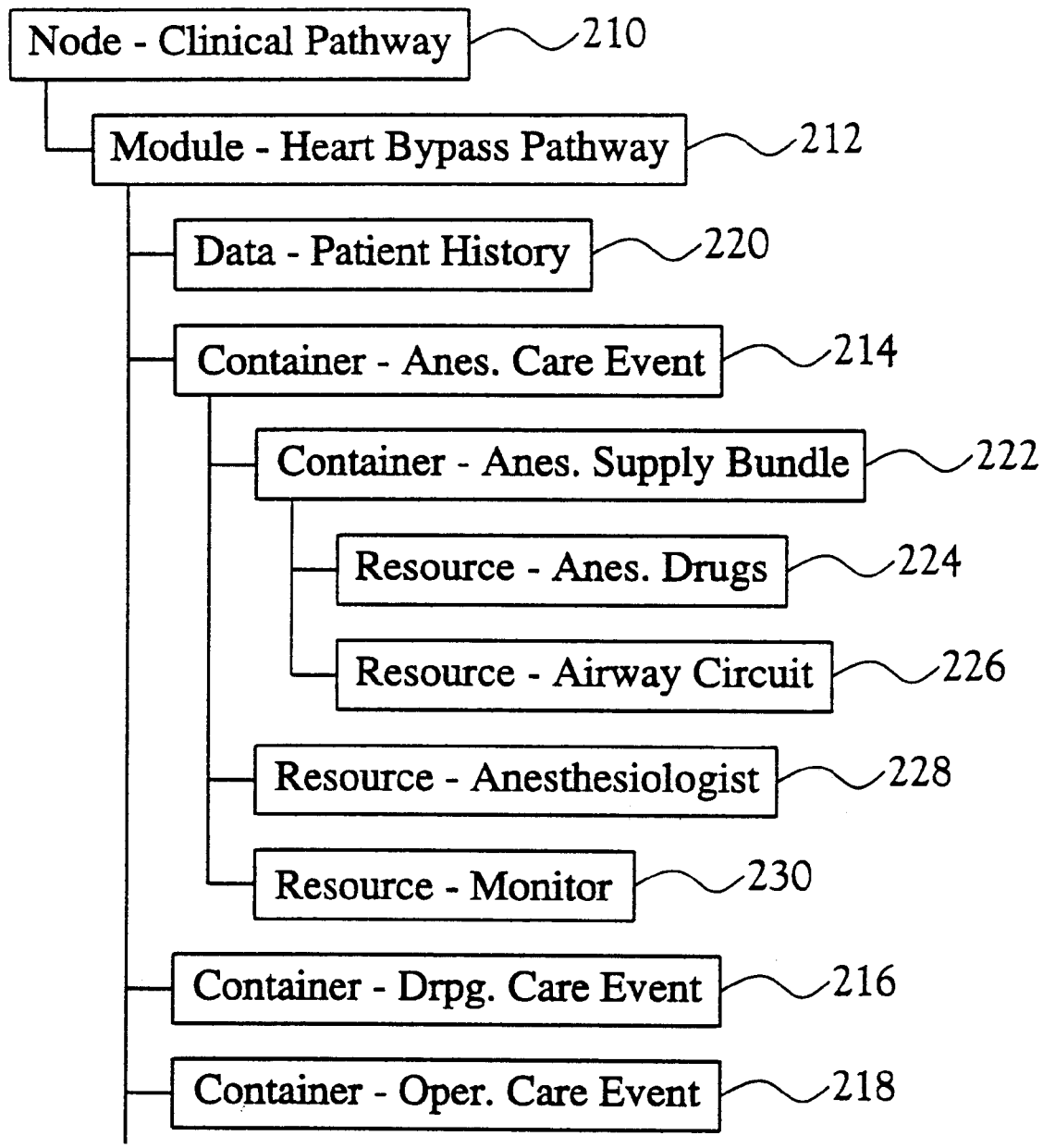
FIG. 2 is a tree diagram showing the organization of a preferred form of the present invention.

Use of the software objects is best understood by with a general reference to one function of the information system. Referring now to FIG. 2, the first node 210 of the software represents the function of generation, modification and maintenance of software templates for clinical pathways using the objects previously described. This node 210 allows the user to create software modules 212, made up of user selected objects, which represent in software a health-care procedure or clinical pathway. In general, as described previously, the clinical pathway will be broken down into a series of related care events, representing discrete sub-procedures along the clinical pathway. Using the functionality provided by the clinical pathway node 210, the user would be able to develop a new module 212 by making the appropriate menu selection. The user would be prompted to input information relevant to the clinical pathway generally, such as the name of the clinical pathway, any hospital or other codes used to identify the type of procedure, doctors who perform that type of procedure, etc.

Once the module 210 is defined and created, the user would then break the procedure down into a series of care events. For example, if the procedure were a heart bypass operation, various care events can be identified such as 1) anesthesia care event, 2) draping care event and 3) the operative care event. Each of these care events would be implemented in the clinical pathway module 212 by the selection or creation of care event container objects corresponding to each care event 214, 216, and 218. These objects would require the input of information relevant to the care event and would function as containers for additional container, resource or data care events.

Once the care event containers 214, 216 and 218 have been created in the module 212, the user would then fill out each of the associated care events for the module. For example, a patient history data object 220 might be associated with the module 212 which would prompt the user to obtain patient specific data when the clinical pathway is used relative to a particular patient. Resources would then be associated with each care event.

For example, the Anesthesia Care Event container 214, may contain an anesthesia supply bundle container 222, which in turn can contain resources such as anesthesia drugs 224 and an airway circuit 226. Other resources, provided by a resource object, such as an anesthesiologist 228 and patient monitor 230, which are related to the anesthesia care event 214 are also associated with the anesthesia care event 230. In the example, the anesthesia drugs resource 224 represents a pharmaceutical resource object, which would contain certain information relevant to the specific drugs to be delivered, while the airway resource 226 represent specific supplies to be used in the anesthesia care event object 214; these two items, because they will be used together, are combined in a supply bundle container 222 which may be reused for other procedures which include an anesthesia care event. The anesthesiologist resource 228 represents a personnel resource object and will contain information concerning the anesthesiologist including identification, time to be allotted for the procedure and scheduling information. The patient monitor resource object 230, represents an equipment resource which would contain information about its availability and utilization.

This process would be repeated until each of the remaining care events 216 and 218 for the clinical pathway was completed (a more complete description of a clinical pathway, including examples of multiple care events which have been completed will be provided in the Description of an Exemplar Embodiment below). The user of the information system would then have a software module 212 configured for the heart bypass clinical pathway which would consist of container, resource and data objects. Each of the software objects would encapsulate information particular to that object and would communicate that information via a standard interface to other software objects as such information is required.

For example, after constructing a particular clinical pathway module, the user might desire to schedule a procedure for a particular patient using the clinical pathway. By utilizing a node designed to manage information for individual cases, the user could select the appropriate clinical pathway module which would transfer the data from the clinical pathway module for that procedure into a case module. The case module would then contain all of the information from the objects from the selected clinical pathway module and would provide a ready listing of resources to be utilized in performing the procedure. With this information, schedules of supplies, equipment, etc. could be generated in order to facilitate the performance of the procedure. Additionally, as will be described more fully hereinafter, by creating a case module, the user would have available the case node functionality which would allow for the tracking of resource utilization in performing the procedure and create a consumption record for use in analyzing resource utilization, generating cost information for cost recovery and allow the user to perform other case node specific functions. Also, to the extent that objects created in the clinical pathway have utility for other clinical pathways, the created objects may be reused to develop additional clinical pathways.

As will be described in greater detail below, the various types of objects are predefined in the overall software system. Container objects are available to represent care events, supply bundles and conditional supply bundles. Each type of container may then be configured by the user to reflect the particulars of the clinical pathway to be represented. Care event containers will be configured with specific information for each care event in the clinical pathway and will contain information relevant to that care event. Supply bundles will be provisioned with supply resource objects and will have information specific to that supply bundle contained therein. Conditional supply bundles will be provisioned with supplies and a condition, which will determine if that conditional supply bundle will be used; for example, a conditional supply bundle may be developed for a particular surgeon and will have supplies used only by that surgeon provided therein. Then, if the condition is met when a case is scheduled, such as the particular surgeon is assigned to the case, that conditional bundle will automatically be added to the list of objects associated with that case.

Similarly various types of resource objects are provided as standard templates for configuration by the user. Examples of such types of resource objects are supplies, kits (which are pre-packaged groups of supplies), equipment, personnel and pharmaceuticals. When configuring resource objects for a clinical pathway, the user would select the appropriate supply type for the resource to be represented and input the prompted information. For example, the user might be able to look up a database of listed supplies and select a particular supply for inclusion in the clinical pathway. Alternatively, the user could create a new supply from scratch by inputting prompted information to create a new supply resource object. The type of information would vary from resource type to resource type, but a standard template would be provided for each resource type to prompt the user to input the appropriate information for each resource to be added.

Additionally, while the user would have the option to create various container, resource and data objects from scratch for use in the information system, the user, to the extent appropriate would be able to reuse previously created objects. For example, the user might create a library of standard pre-configured objects which would be frequently re-used in various clinical pathways. Thus, when a new pathway was being created, these library objects may be selected for inclusion in the new pathway. Likewise, information concerning a variety of resources may be maintained in various database systems maintained by a healthcare institutions. The supply department may maintain a database of available supplies, or dealers may provide databases of available supplies, by providing standard database program interfaces for these sources of information, data from these source may be automatically read into the present system in order to configure resource software objects for use therein.

As described, the use of software objects to represent events, bundles, resources and data objects in a health-care information management system allows the user to readily create software modules which represent specific health-care procedures which are much more functional then with traditional health-care database systems. Furthermore, the module object approach to the system makes it more readily customizable for particular installations. For example, if the standard configuration of any software object is not readily adapted for a particular installation, a programmer will not be required to modify a monolithic source code listing to implement the new configuration. For customization, the programmer will only have to rewrite the code for a particular object. As long as the programmer retains the standardized data interface for the object, there will not need to be any change in configuration in the remaining source code for the system.

Additionally, the use of the software object framework allows for the ready implementation of new functionality, without requiring the rewrite of the majority of the code for the system. For example, if a new functionality is required, a new functional node may be added which will utilize, to the extent possible, already existing software objects. One example might be to add a scheduling node to the above described software to allow for the ready scheduling of personnel, equipment, supplies, etc. Most of the scheduling information for any given procedure will be available in the clinical pathway module for that procedure. Thus, to create a scheduling node, all the programmer would need to do is create a software object which would query existing objects for data relevant to scheduling and organize that data in a useful manner. In the context of the present invention, such a node could create scheduling objects for various resources indicating their utilization schedule (as received from the object representing such resources) which would automatically query scheduled resources, check their availability and establish a calendar for each. Other functionality could be created by the creation of other nodes.

For example the functionality of tracking resource utilization in the manner described in application Ser. No. 08/846,798, filed Apr. 30, 1997, entitled, Method and System for the Tracking and Profiling of Supply Usage in a Health Care Environment, may be provided as a functional node software object. In implementing such a node, each individual procedural pathway as described in that application may be copied from a clinical pathway constructed as described above with reference to FIG. 2. A further type of node functionality is described in U.S. patent application Ser. No. 08/936,780, filed Sep. 24, 1997, entitled Method for the Analysis and Standardization of Bills of Resources which would provide from the conversion of case software module objects into models which could then be analyzed for resource utilization efficiency and the standardization of bills of resource. Furthermore, the output of the node functionality described in application Ser. No. 08/936,780, could then be used to create an optimized clinical pathway under the clinical pathway node described with reference to FIG. 2.

The functionality described above is implemented in the Meridian™ information management system marketed by DeRoyal Business Systems, 200 DeBusk Lane, Powell, Tenn., 37849, which is an affiliate of the assignee hereof, DeRoyal Industries, Inc.

The foregoing description of the preferred embodiment of the present invention is for the purposes of illustration and not limitation. The preferred embodiment is capable of numerous modifications, substitutions and deletions without departing from the scope of the invention as set forth in the following claims. For example, while the preferred embodiment is described as being implemented in the Windows 95® or NT® environment using ActiveX® or OLE® controls from Microsoft Corp., the modular software object approach described could be implemented in other standards or operating environments such as Delphi®. Furthermore, while the objects described above are preferentially written in Visual C++, any other common programming language may be used as well. Finally, the computer environment is preferentially a PC environment, either networked or stand-alone, other computer systems such as RISC servers, workstations, mainframes, or access to processors through the Internet may be substituted.

We claim:

1. An information management system for managing information relating to supplying, scheduling, logging, and analyzing use of health care services resources, the system comprising:

a general purpose computer system, including;
storage means for storing data corresponding to the information,
processing means for processing instructions relating to managing the information,
display means for presenting the information in a human perceptible format, and
input means for receiving user input relating to managing the information,
information management software installed on the general purpose computer system, including;
node software objects, each of the node software objects providing a health-care information management function, including;
a clinical pathway node software object for selectively creating, managing, and maintaining user-defined, user-configurable clinical pathway module software objects adapted to function with the clinical pathway node software object and representing template sets of the information relating to health care services procedures, the module software objects including, resource software objects, corresponding to resources to be used in providing health care services, and
container software objects for containing software objects having at least one common characteristic,
a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient specific information, and a standardization review node software object for selectively creating, managing, and maintaining a user-defined, user-configurable model module software object adapted to function with the standardization review node software object from the case management module software object, the model module software object representing a case management module software object as modified by at least the patient-specific information to reflect a historical patient-specific case, the standardization review node software object further being suitable for selectively creating, managing, and maintaining a user-defined, user-configurable utilization study module software object from at least one model module software object, and the standardization review node software object further being suitable for analyzing the utilization study module software object to detect trends in the health care services information.

2. The system of claim 1 wherein the container software objects comprise a plurality of container software object types, each type providing a specific container software object functionality.

3. The system of claim 1 wherein the container software objects comprise:

a user-configurable care event container software object representing a specific health care services care event, the care event container software object functional to contain container software objects and resource software objects related to the specific health care services care event represented by the care event container software object, and a user-configurable bundle container software object functional to contain resource software objects corresponding to specific related health care resources which would be provided in a group or bundle.

4. The system of claim 1 further comprising data software objects selectively associated with a software object selected from the group consisting of the clinical pathway module software object, the case management module software object, and the container software object, the data software objects suitable for collecting and maintaining information related to the software object with which the data software object is selectively associated.

5. The system of claim 1 further comprising a library node software object for selectively creating, collecting, and organizing reusable, user-defined, user-configurable container software objects and resource software objects for use in the clinical pathway node software object and the case management node software object.

6. An information management system for managing information relating to supplying, scheduling, logging, and analyzing use of health care services resources, the system comprising:

a general purpose computer system, including;

storage means for storing data corresponding to the information, processing means for processing instructions relating to managing the information, display means for presenting the information in a human perceptible format, and input means for receiving user input relating to managing the information, information management software installed on the general purpose computer system, including;

node software objects, each of the node software objects providing a health-care information management function, including;

a clinical pathway node software object for selectively creating, managing, and maintaining user-defined, user-configurable clinical pathway module software objects adapted to function with the clinical pathway node software object and representing template sets of the information relating to health care services procedures, the module software objects including, resource software objects, corresponding to resources to be used in providing health care services, container software objects for containing software objects having at least one common characteristic, wherein the container software objects comprise a plurality of container software object types, each type providing a specific container software object functionality, including, a user-configurable care event container software object representing a specific health care services care event, the care event container software object functional to contain container software objects and resource software objects related to the specific health care services care event represented by the care event container software object, and a user-configurable bundle container software object functional to contain resource software objects corresponding to specific related health care resources which would be provided in a group or bundle, and data software objects selectively associated with a software object selected from the group consisting of the clinical pathway module software object, the case management module software object, and the container software object, the data software objects suitable for collecting and maintaining information related to the software object with which the data software object is selectively associated, a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient specific information, a standardization review node software object for, selectively creating, managing, and maintaining a user-defined, user-configurable model module software object adapted to function with the standardization review node software object from the case management module software object, the model module software object representing a case management module software object as modified by at least the patient-specific information to reflect a historical patient-specific case, selectively creating, managing, and maintaining a user-defined, user-configurable utilization study module software object from at least one model module software object, and analyzing the utilization study module software object to detect trends in the health care services information, and a library node software object for selectively creating, collecting, and organizing reusable, user-defined, user-configurable container software objects and resource software objects for use in the clinical pathway node software object and the case management node software object.

* * * * *